US00PP22794P2

(12) United States Plant Patent
Pitiot et al.

(10) Patent No.: US PP22,794 P2
(45) Date of Patent: Jun. 19, 2012

(54) APPLE TREE NAMED 'INORED'

(50) Latin Name: ***Malus domestica* Borkh**
Varietal Denomination: Inored

(75) Inventors: Christelle Pitiot, Lyons (FR); François Laurens, Beaucouze (FR)

(73) Assignees: Institut National de la Recherche Agronomique, Paris (FR); Novadi SARL, Lyons (FR)

( * ) Notice: Subject to any disclaimer, the term of this patent is extended or adjusted under 35 U.S.C. 154(b) by 0 days.

(21) Appl. No.: 12/932,658

(22) Filed: Mar. 1, 2011

(51) Int. Cl.
*A01H 5/00* (2006.01)

(52) U.S. Cl. ..... Plt./161

(58) Field of Classification Search ..... Plt./161
See application file for complete search history.

*Primary Examiner* — Annette Para
(74) *Attorney, Agent, or Firm* — Michelle Bos

(57) ABSTRACT

'Inored' is a new apple tree notable for its resistance to scab, and for its high quality fruit. Fruit of 'Inored' is highly colored, sweet, and late-maturing and has a long shelf life.

6 Drawing Sheets

Latin name: *Malus domestica* Borkh.
Variety denomination: 'Inored'.

BACKGROUND OF THE VARIETY

'Inored' is a new and distinct cultivar of apple tree (*Malus domestica* Borkh). This new cultivar is a product of a controlled cross of 'Pinova' (U.S. Plant Pat. No. 11,601) ×'X6398' (not patented), carried out at Angers, France in 1995. 'Inored' was initially selected for propagation and further experimentation because of its attractive fruit and resistance to common strains of scab. The first asexual reproduction of the variety took place at Jonquieres, France in 1998, by grafting. 'Inored' has been observed to remain true to type over successive asexually propagated generations.

BRIEF DESCRIPTION OF THE VARIETY

'Inored' is a new apple tree notable for its resistance to scab, and for its high quality fruit. Fruit of 'Inored' is highly colored, sweet, and late-maturing and has a long shelf life. The new variety is distinguished from female parent 'Pinova' by its more globose fruit shape, highly colored fruit, late maturity (14 days after 'Pinova') and scab resistance. 'Inored' is distinguished from 'X6398' by its highly colored fruit, improved shelf life, and late maturity (14 days after 'X6398').

BRIEF DESCRIPTION OF THE PHOTOGRAPHS

Figure 1:
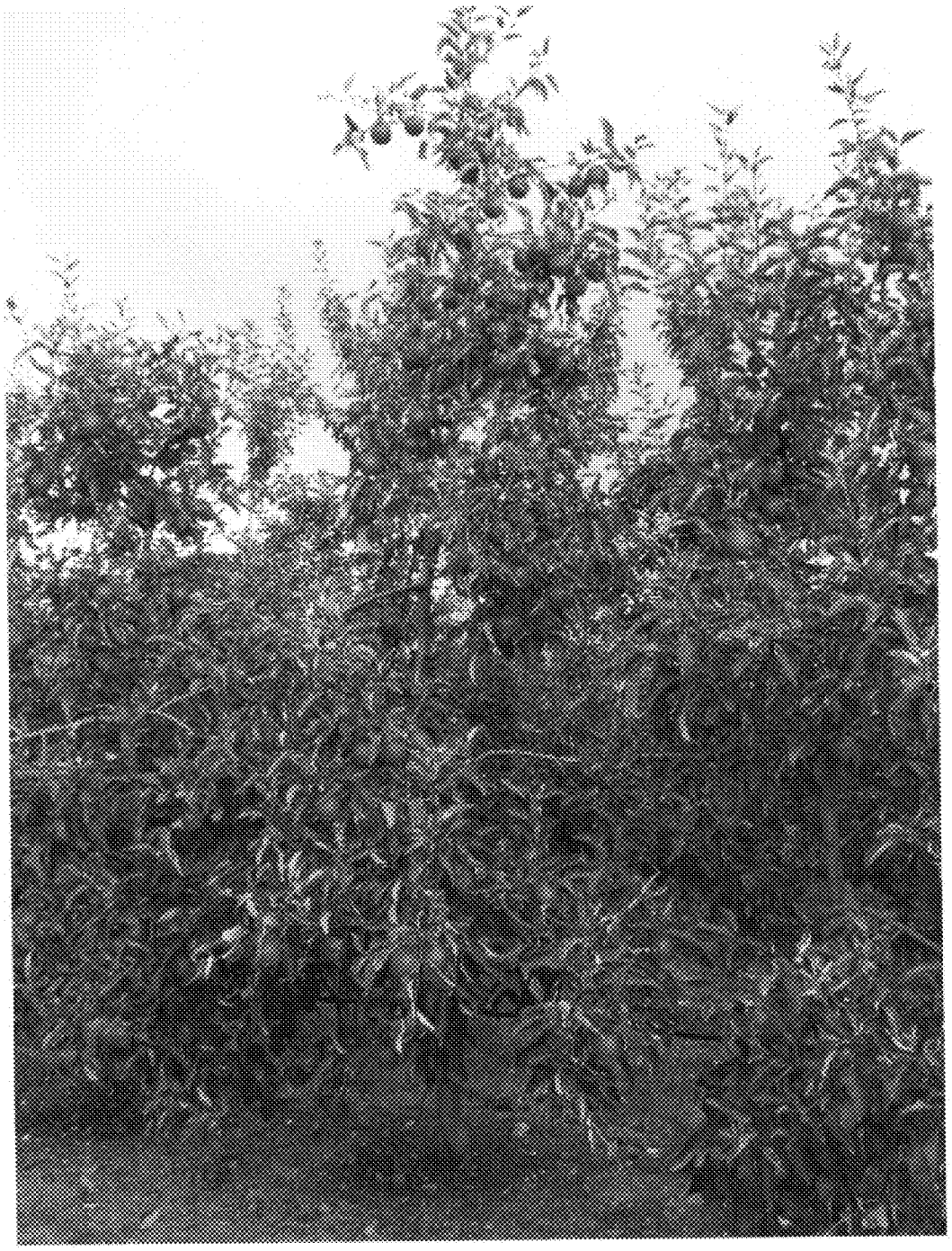
Figure 2:
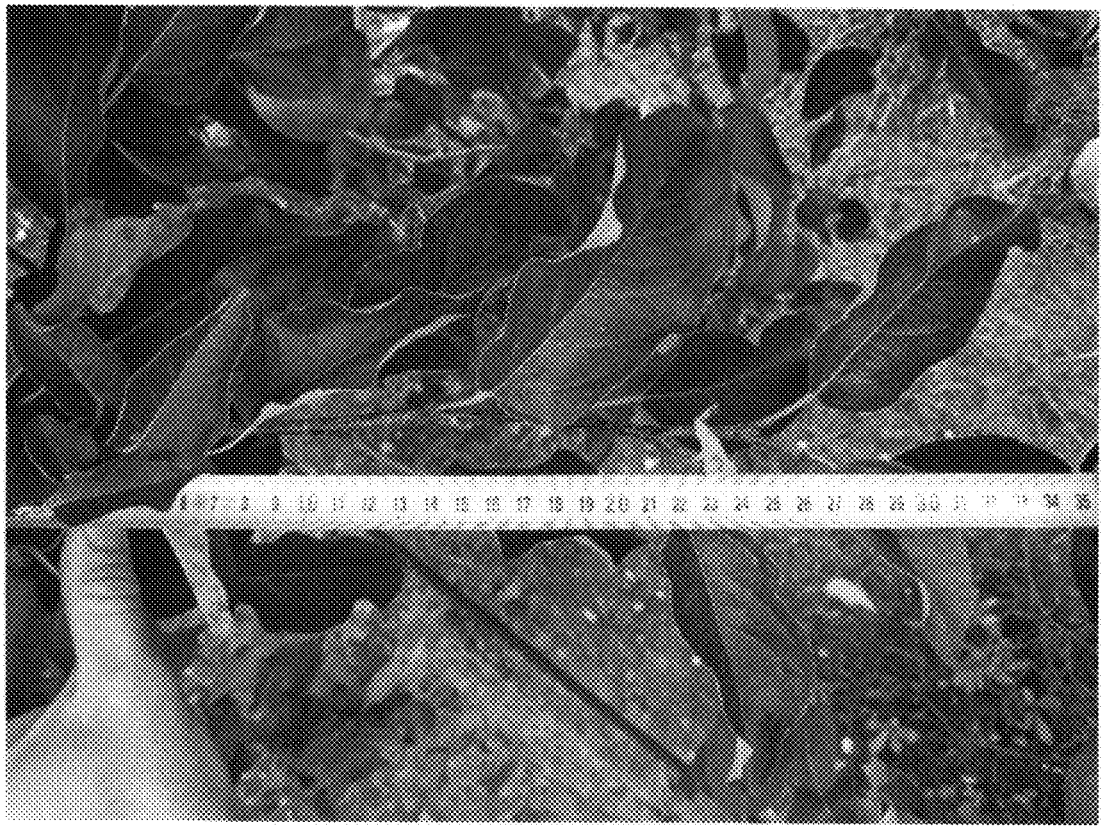
Figure 3:
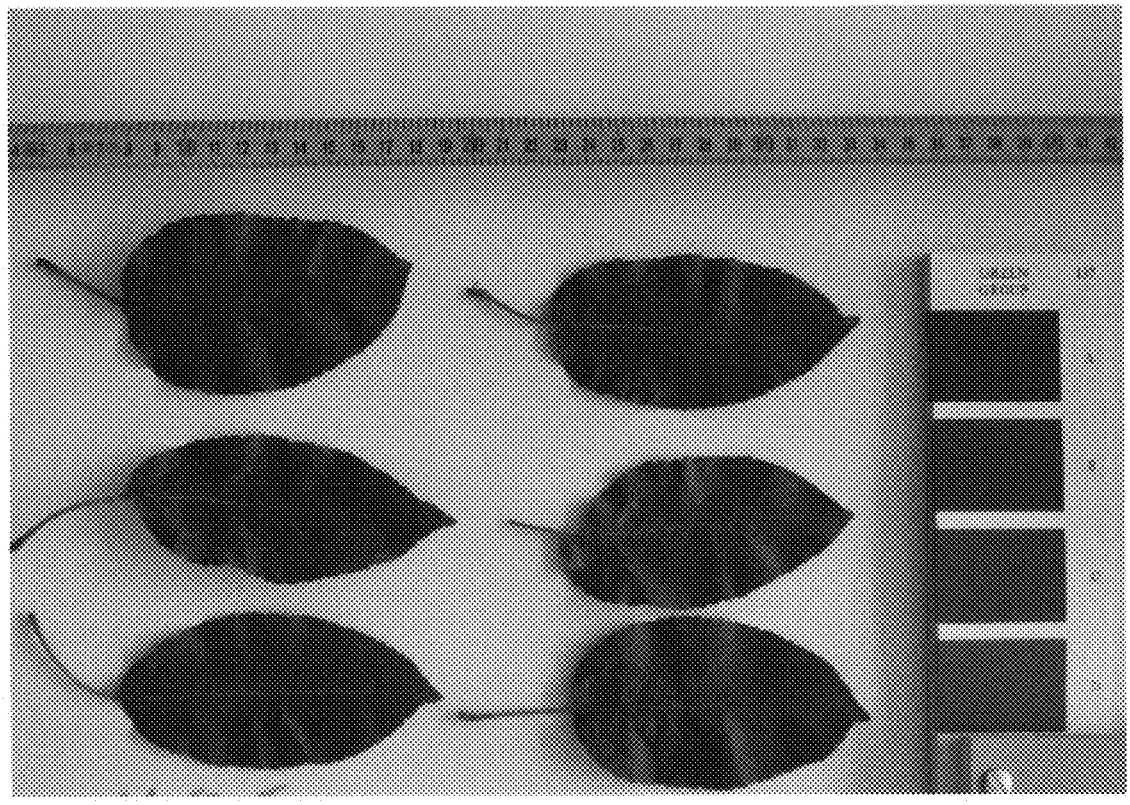
Figure 4:
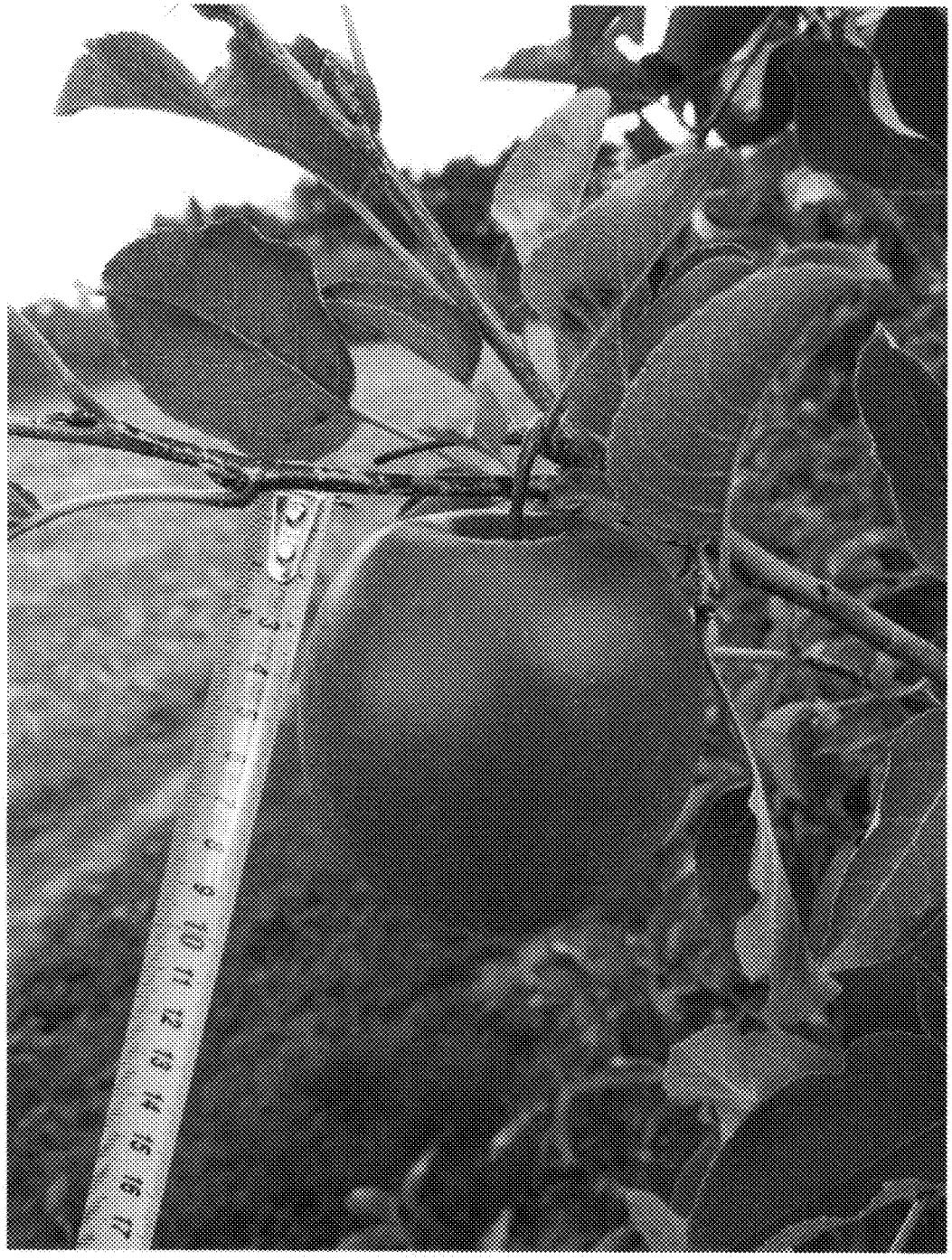
Figure 5:
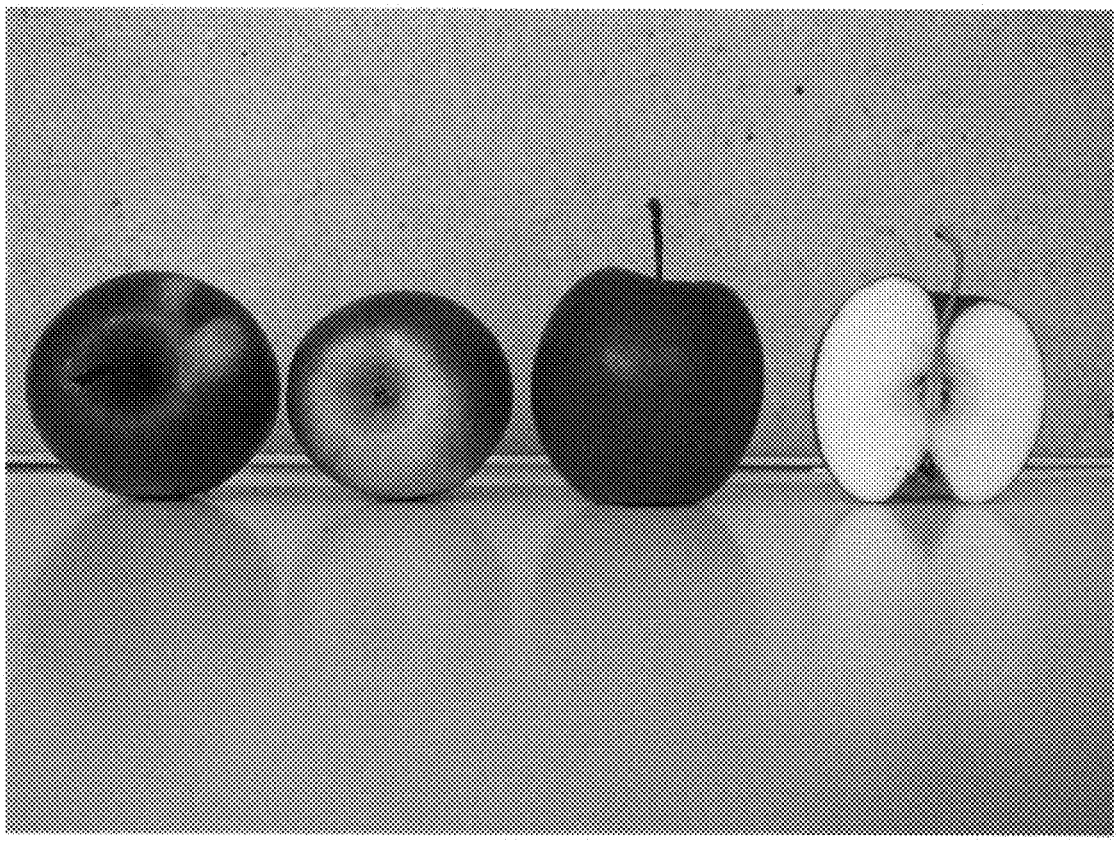
Figure 6:
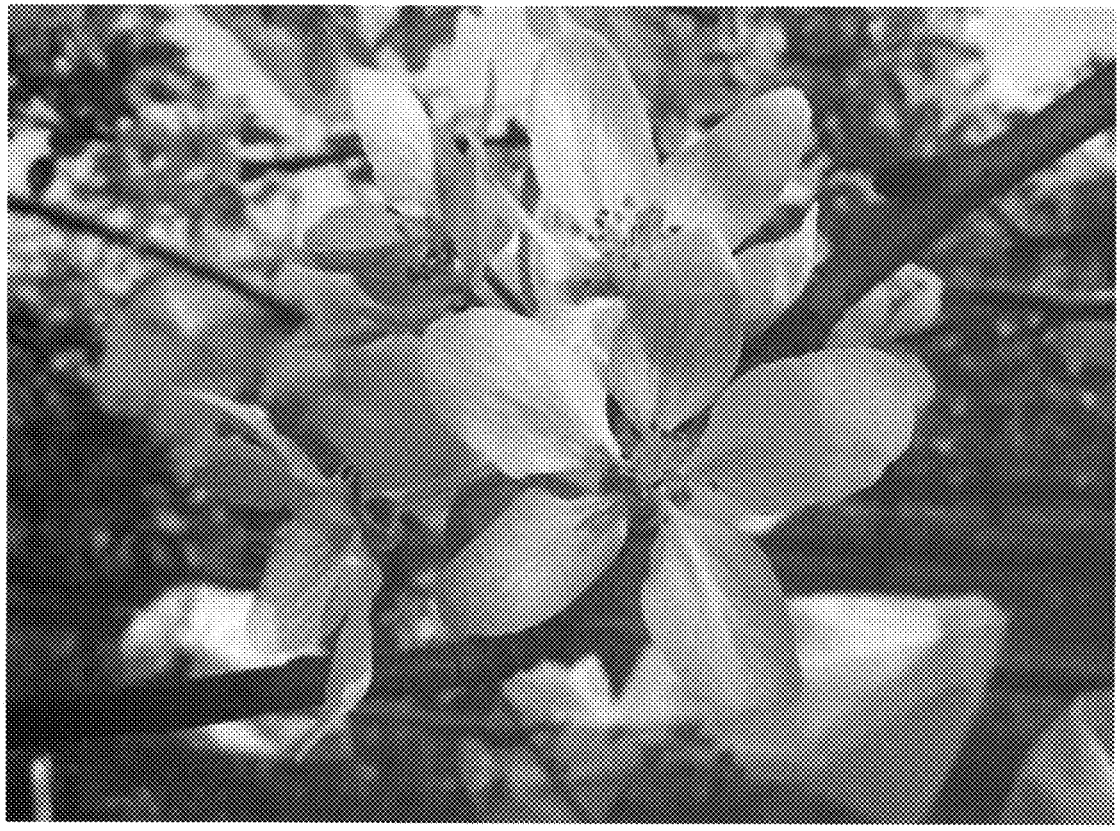

FIG. 1 shows a tree of the new variety;
FIG. 2 shows a branch and leaves of the new variety;
FIG. 3 shows the leaves of the new variety;
FIG. 4 shows a fruit of the new variety; and
FIG. 5 shows whole and sectioned fruit of the new variety.

DETAILED BOTANICAL DESCRIPTION OF THE VARIETY

The following-detailed botanical description is based on observations of trees of 'Inored' in their sixth leaf. The trees were grown at Querré, France on Pajam®2 Cepiland rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Average.
- *Type.*—Spreading to weeping.
- *Height.*—3.60 m.
- *Diameter.*—1.3 m.
- *Trunk diameter* (30 *cm above graft union*).—62 mm.
- *Bark texture.*—Rough.
- *Bark coloration.*—Greyed-green 197B.
- *Lenticels.*—Orange-white 159A; height 0.85 mm (+/−10%); Length 2 to 5 mm.

Branch (fruiting branches located at around 1 m above the graft union):
- *Length.*—1.20 m (+/−10%).
- *Diameter.*—23 cm.
- *Crotch angle.*—90°.
- *Coloration.*—Grey 201B.
- *Lenticels.*—Orange-white 159A; height 0.7 mm; length 1 to 2 mm; 3 to 6 per $cm^2$.

1 Year old shoot:
- *Length.*—25 cm.
- *Coloration.*—Greyed-purple 183A.
- *Pubescence.*—Weak.
- *Thickness.*—4.2 mm.
- *Internode length.*—4.5 cm.
- *Lenticels.*—Yellow-white 158B; height 0.5 mm; length 0.8 to 1 mm; 6 to 8 per $cm^2$.

Winter hardiness:
- *Hardiness* (*climate suitability*).—Temperate.

Flowers:
- *Color* (*balloon stage*).—Greyed-purple 186B.
- *Diameter of open flower.*—50 mm.
- *Relative position of petal margin.*—Touching.
- *Number per cluster.*—5 to 6.

Petals:
- *Number per flower.*—5.
- *Shape.*—Oval.

*Length*.—25 mm.
*Width*.—16 mm.
*Apex*.—Rounded.
*Base*.—Cuneate.
*Margin*.—Smooth.
*Color—upper surface*.—Pink 56D.
*Color—lower surface*.—Pink 186D.
*Pistils*.—Length 4 to 5 mm, yellow-green 145C.
*Anthers*.—About 20, length 2 mm, pollen yellow 10B.
*Stigma*.—0.6 mm, greyed-yellow 160B.
*Style*.—Length 7 to 8 mm, yellow-green 145C.
*Ovary*.—Length 3 mm, pubescent.
*Pedicel*.—Length 3 mm, diameter 1.2 mm, yellow-green 146B/C.
*Sepals*.—Quantity 5, length 8 to 9 mm, color yellow-green 144B.

Leaves:
*Shape*.—Oblong.
*Length* (*petiole not included*).—10.9 cm.
*Width*.—5.6 cm.
*Blade margin*.—Serrate to crenate.
*Apex shape*.—Acuminate.
*Base shape*.—Rounded.
*Coloration of top surface*.—Green 137A.
*Coloration of bottom surface*.—Yellow-green 148B.
*Attitude in relation to shoot*.—Upright.

Petiole:
*Length*.—3 cm.
*Diameter*.—1.9 mm.
*Coloration*.—Yellow-green 144C.

Fruit:
*Quantity per cluster*.—1 to 2.
*Size*.—75 to 80 mm.
*Weight*.—200 g.
*General shape in profile*.—Ellipsoid.
*Position of maximum diameter*.—In the middle of the fruit.
*Ribbing*.—Weak.
*Crowning at calyx end*.—Weak to average.
*Aperture of eye*.—Average.
*Size of eye*.—8 mm.
*Length of sepal*.—6 to 8 mm.
*Depth of eye basin*.—10.2 mm.
*Width of eye basin*.—30 mm.
*Length of stalk*.—40 mm.
*Thickness of stalk*.—2 mm.
*Width of stalk cavity*.—33 mm.
*Depth of stalk cavity*.—15 mm.
*Size of lenticels*.—0.5 mm.
*Bloom of skin*.—Light.
*Greasiness of skin*.—Weak.
*Background colour of skin*.—Yellow-green 154D.
*Over colour of skin*.—Red 46A.
*Amount of over colour*.—75% to 100%.
*Intensity of over colour*.—Bright.
*Pattern of over colour*.—Solid flush with weakly defined stripes.
*Flesh texture*.—Average fineness.
*Aroma*.—Sweet.
*Juiciness*.—Average.
*Brix*.—13° to 15°.
*Flesh coloration*.—Yellow 4D.
*Stem coloration*.—Greyed-purple 183A.

Seeds:
*Quantity per fruit*.—7.
*Shape*.—Long, narrow and pointed.
*Coloration*.—Greyed-orange 177A.

Harvest:
*Amount of fruit produced per tree per harvest*.—22 to 25 kg.
*Harvest date range*.—October 7 to 9.

Diseases/pests:
*Resistance*.—Common races of scab (VF).
*Susceptibility*.—Powdery mildew.

Market use: Fresh market.

We claim:

1. A new and distinct apple tree substantially as described and illustrated herein.

* * * * *